United States Patent
Raichelgauz et al.

(10) Patent No.: US 11,543,360 B2
(45) Date of Patent: Jan. 3, 2023

(54) IDENTIFYING AND GRADING DIAMONDS

(71) Applicant: Cortica Ltd., Tel Aviv (IL)

(72) Inventors: Igal Raichelgauz, Tel Aviv (IL); Karina Odinaev, Tel Aviv (IL)

(73) Assignee: Cortica Ltd., Tel Aviv (IL)

( * ) Notice: Subject to any disclaimer, the term of this patent is extended or adjusted under 35 U.S.C. 154(b) by 217 days.

(21) Appl. No.: 16/942,712

(22) Filed: Jul. 29, 2020

(65) Prior Publication Data
US 2021/0003510 A1 Jan. 7, 2021

Related U.S. Application Data

(60) Provisional application No. 62/869,565, filed on Jul. 2, 2019.

(51) Int. Cl.
| | |
|---|---|
| *G01N 21/87* | (2006.01) |
| *G01N 33/38* | (2006.01) |
| *G06V 10/56* | (2022.01) |
| *G06K 9/62* | (2022.01) |
| *G01J 3/46* | (2006.01) |
| *G01N 21/95* | (2006.01) |
| *G06V 10/42* | (2022.01) |
| *G06V 10/75* | (2022.01) |
| *B07B 13/00* | (2006.01) |

(52) U.S. Cl.
CPC ............ *G01N 21/87* (2013.01); *B07B 13/003* (2013.01); *G01J 3/463* (2013.01); *G01N 21/9515* (2013.01); *G01N 33/381* (2013.01); *G06K 9/627* (2013.01); *G06K 9/6215* (2013.01); *G06V 10/421* (2022.01); *G06V 10/56* (2022.01); *G06V 10/751* (2022.01); *G06K 9/6218* (2013.01)

(58) Field of Classification Search
CPC .. G01N 21/87; G01N 21/9515; G01N 33/381; B07B 13/003; G01J 3/463; G06K 9/6215; G06K 9/627; G06K 9/6218; G06V 10/421; G06V 10/56; G06V 10/751
See application file for complete search history.

(56) References Cited

U.S. PATENT DOCUMENTS

| | | | | |
|---|---|---|---|---|
| 4,601,395 A | * | 7/1986 | Juvinall | ................... B07C 5/126 209/939 |
| 6,239,867 B1 | * | 5/2001 | Aggarwal | .............. G01N 21/87 356/30 |
| 6,980,283 B1 | * | 12/2005 | Aggarwal | .............. G01N 21/87 356/30 |
| 8,270,762 B1 | * | 9/2012 | Abel | ......................... G09G 3/02 382/128 |
| 9,222,893 B2 | * | 12/2015 | Hornabrook | ......... G01N 33/381 |
| 2006/0074588 A1 | * | 4/2006 | Blodgett | .............. A44C 17/001 702/179 |

(Continued)

*Primary Examiner* — Violeta A Prieto
(74) *Attorney, Agent, or Firm* — Reches Patents

(57) ABSTRACT

A method for generating a highly distinctive signature of a certain diamond, the method may include generating, based on one or more images of the certain diamond, a certain diamond signature of the certain diamond; finding, out of a group of reference diamonds, other diamonds having other diamond signatures; wherein the finding comprises calculating similarities between the certain diamond signature and reference diamond signatures of the reference diamonds of the group; and generating a new certain diamond signature that significantly differs from signatures of the other diamonds.

15 Claims, 5 Drawing Sheets

(56) References Cited

U.S. PATENT DOCUMENTS

| | | | |
|---|---|---|---|
| 2007/0294187 A1* | 12/2007 | Scherrer | G06Q 20/401 |
| | | | 705/75 |
| 2008/0006615 A1* | 1/2008 | Rosario | B23K 26/032 |
| | | | 219/121.68 |
| 2010/0010751 A1* | 1/2010 | Blodgett | A44C 17/001 |
| | | | 356/30 |
| 2010/0010752 A1* | 1/2010 | Blodgett | A44C 17/001 |
| | | | 356/30 |
| 2010/0111354 A1* | 5/2010 | Hornabrook | G01N 21/87 |
| | | | 356/30 |
| 2018/0156735 A1* | 6/2018 | Fitch | G01N 21/25 |
| 2018/0342053 A1* | 11/2018 | Balagurusamy | G06T 7/55 |
| 2021/0148831 A1* | 5/2021 | Raichelgauz | G06V 10/421 |
| 2021/0293729 A1* | 9/2021 | Connell | G01N 33/24 |

\* cited by examiner

PRIOR ART

Color grading

Clarity grading

IDENTIFYING AND GRADING DIAMONDS

CROSS REFERENCE

This application claims priority from U.S. provisional patent 62/869,565 filing date Jul. 2, 2019.

BACKGROUND

One of the first things most people learn about diamonds is that not all diamonds are created equal. In fact, every diamond is unique. Diamonds come in many sizes, shapes, colors, and with various internal characteristics.

All polished diamonds are valuable. That value is based on a combination of factors. Rarity is one of those factors. Diamonds with certain qualities are rarer—and more valuable—than diamonds that lack them.

Today, diamonds are evaluated manually in a biased and error prone process.

There is a growing need to provide a highly accurate method for diamond evaluation.

SUMMARY

There may be provided systems, methods and computer readable medium as illustrated in the specification.

BRIEF DESCRIPTION OF THE DRAWINGS

The embodiments of the disclosure will be understood and appreciated more fully from the following detailed description, taken in conjunction with the drawings in which.

DESCRIPTION OF EXAMPLE EMBODIMENTS

Figure 1:
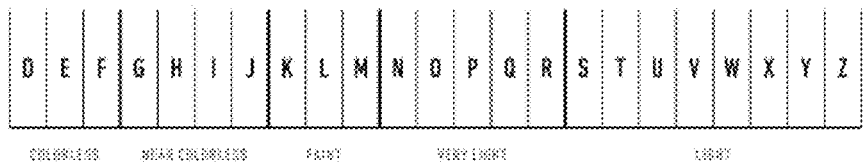
FIG. 1 illustrates prior art grades.
Figure 1:
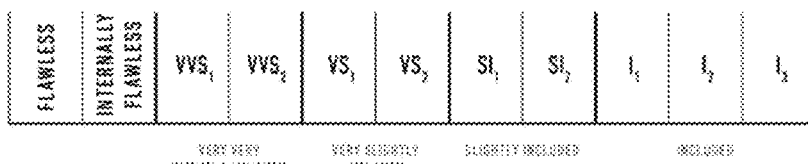

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a device or system capable of executing the method and/or to a non-transitory computer readable medium that stores instructions for executing the method.

Any reference in the specification to a system or device should be applied mutatis mutandis to a method that may be executed by the system, and/or may be applied mutatis mutandis to non-transitory computer readable medium that stores instructions executable by the system.

Any reference in the specification to a non-transitory computer readable medium should be applied mutatis mutandis to a device or system capable of executing instructions stored in the non-transitory computer readable medium and/or may be applied mutatis mutandis to a method for executing the instructions.

Any combination of any module or unit listed in any of the figures, any part of the specification and/or any claims may be provided.

The terms "parametric signature" and "diamond signature" are used in an interchangeable manner.

The specification and/or drawings may refer to a diamond. A diamond is an example of a precious gem.

The signature may be generated and/or matching signatures can be searched and/or concept structures can be provided in various manners—for example—in any manner illustrated in at least one out of U.S. patent application Ser. No. 16/544,940 filing date Aug. 20, 2019, PCT patent application PCT/IB2019/058207 filing date Sep. 29, 2019, and U.S. patent application Ser. No. 16/544,940 filing date Dec. 28, 2019—all being incorporated herein by reference.

The specification and/or drawings may refer to an image. An image is an example of sensed information. The sensed information can be any reading of any sensors—including any radiation sensor (x-ray sensor, infrared sensor, visible light sensor, and the like).

The properties of a diamond may be measured in any manner For example—some properties are measured according to certain standards, well known specifications, and the like.

Examples of some of the measured properties of diamonds may include color, clarity and cut.

Color

Subtle differences in color can dramatically affect diamond value. Two diamonds of the same clarity, weight, and cut can differ in value based on color alone. Even the slightest hint of color can make a dramatic difference in value.

In the normal color range, the closer a diamond gets to colorless, the higher its per-carat price. There's an especially large leap in the price of a colorless diamond, which is extremely rare.

The color may be represented by letters D-Z, whereas D is the most colorless diamond and Z is the most colored diamond. D-F represent colorless diamonds, G-J represent near colorless diamonds, K-M represent faint diamonds, N-R represent very light diamonds and S-Z represent light diamonds.

The GIA graders follow a strict protocol that dictates the type of lighting and neutral background used, as well as precisely how the diamond should be held and viewed during the assessment. A color grade is determined by comparing the diamond to master stones—a set of color-comparison diamonds of known position on the GIA D-to-Z color grading scale—when all are placed table down in a grading tray. This viewing position reduces the complex appearance of a faceted colorless to near-colorless diamond when viewed face up.

Clarity

Few things in nature are absolutely perfect. This is as true of diamonds as anything else. Diamonds have internal features, called inclusions, and surface irregularities, called blemishes. Together, they're called clarity characteristics. Clarity is the relative absence of inclusions and blemishes.

Among other things, blemishes include scratches and nicks on a diamond's surface. Inclusions are generally on the inside, and some might break the surface of the stone. Sometimes, tiny diamond or other mineral crystals are trapped inside a diamond when it forms. Depending on where they're located, they might remain after the stone has been cut and polished, and they can affect a diamond's appearance.

Clarity characteristics might have a negative influence on a diamond's value, but they can have positive effects as well. For one thing, they help gemologists separate diamond from imitations. (This is easier with included diamonds than with flawless ones.) And because no two diamonds have exactly the same inclusions, they can help identify individual stones. They can also provide scientists with valuable information about how diamonds form.

No two diamonds have exactly the same clarity characteristics in exactly the same locations. This fact helps gemologists identify individual diamonds.

Like the rest of the 4Cs, clarity's influence on value is directly related to the concept of rarity. Flawless is the top grade in the GIA Clarity Grading System. Diamonds graded Flawless don't have visible inclusions or blemishes when examined under 10-power (10×) magnification by a skilled and experienced grader.

The GIA clarity scale and the color scale are shown in FIG. 1.

For example, an inclusion off to the side of a stone would have less impact on clarity than the same size inclusion located directly under the table. In this case, the position is probably the determining factor.

Cut

Brightness—internal and external white light reflected from a diamond. As a general rule, the higher the cut grade, the brighter the diamond. Under fluorescent lighting, these diamonds (left to right) display high, moderate, and low brightness.

Fire—the scattering of white light into all the colors of the rainbow.

Scintillation—the sparkle a diamond produces, and the pattern of light and dark areas caused by reflections within the diamond.

Weight—the first is the precision with which diamonds are weighed. Diamond weights are stated in metric carats, abbreviated "ct." One metric carat is two-tenths (0.2) of a gram—just over seven thousandths (0.007) of an ounce. One ounce contains almost 142 carats. A small paper clip weighs about a carat.

The metric carat is divided into 100 points. A point is one hundredth of a carat.

Diamonds are weighed to a thousandth (0.001) of a karat and then rounded to the nearest hundredth, or point. Fractions of a carat can mean price differences of hundreds—even thousands—of dollars, depending on diamond quality.

Over a carat, diamond weights are usually expressed in carats and decimals. A 1.03-carat stone, for example, would be described as "one point oh three carats," or "one oh three." Weights for diamonds that weigh under a carat are usually stated in points. A diamond that weighs 0.83 carat is said to weigh "eighty-three points," or called an "eighty-three pointer."

There may be provided a computerized method for determining a grade of a diamond, the method may include generating, by a signature generator, a signature of the diamond; searching, out of multiple concept structures, for a matching concept structures that may include at least one reference signature that matches the signature of the diamond; wherein each concept structure may include diamond signatures of the same grade; wherein at least two concept structures differ from each other by grade; wherein each concept structure may be generated by applying an unsupervised learning process and associating a grade with the cluster; and determining the grade of the diamond based on a grade associated with a matching concept structure.

Each concept structure may be associated with a unique grade that differs from grades of other concept structures.

The signature of the diamond may be indicative of at least one out of

The signature of the diamond may be indicative of at least two out of cut, color, and clarity.

The signature of the diamond may be indicative of cut, color, and clarity.

One or more concept structures may include reference signatures of a same diamond obtained under different image acquisition parameters.

One or more concept structures may include reference signatures of a same diamond obtained under different angles of view.

One or more concept structures may include reference signatures of a same diamond obtained at different points in time.

The method may include generating the multiple concept structures.

The generating may include clustering, in a supervised manner, reference signatures of a same grade to provide the multiple concept structures.

Each cluster may include reference signatures that are of a same unique combination of grade and at least one diamond property.

At least one diamond property may be at least one out of cut, color, and clarity.

Image Based Identification

At least some of the diamond parameters may be obtained by processing a certain image. The weight may be a parameter not identified by an image. Different parameters may be deducted based on one or more images. The images may differ from each other by one or more illumination parameter, one or more collection parameter and/or one or more feature of the sensor that detected the radiation. For example one or more images may be used for determining clarity, one or more other images may be used for determining color and one or more other images may be used to determine cut parameters.

Parameter signatures of a first plurality of images (and optionally weight or any other parameter not obtained by image processing) may be obtained and their combination (or a combination of at least some of the first plurality of images) may form a diamond identifier (that may include one or more diamond signatures).

Parameter signatures of a subset of the first plurality of images (and optionally weight or any other parameter not obtained by image processing) may be used to provide a diamond identifier—thereby allowing the identify the diamond even if one or more images of the first subset are missing. The certainty of identification using a subset is lower than the certainty obtained by using all the first plurality of images.

The parameter signature (and optionally weight or any other parameter not obtained by image processing) may be merged to a single identifier. The merge may be done using a cortex mechanism or by any other process.

A secure data structure may store identifiers of diamonds and it may be accessed with obtained data regarding a certain diamond for identifying the diamond.

Evaluation that Involves Providing Scores to Every Parameter

Each parameter of the diamond can be evaluated separately and get a separate score.

Each parameter of the diamond can be evaluated with different tools (e.g. color—with UV light, clarity under a 10× microscope etc).

Obtain one or more pictures of examples of many diamonds under a microscope (for example a ×10 magnification microscope—although other magnifications may be used) with the evaluation (for example human evaluation) they got (no need an explanation why they got what they got).

The evaluation of diamond may include generating clusters of signatures and their related metadata.

A cluster may include signatures associated with the same grade and identify diamonds that exhibit a unique feature (for example have a unique defect, have a unique cut, and the like).

A cluster may include cluster signatures that may represent a single parameter of the diamond (thus may include one or more parameter signatures), may represent multiple parameters of a diamond.

For example—the clustering may form a cluster of signatures of round defects, may form a cluster of signatures of defects of various sizes, may form cluster of signatures of various locations together, may form cluster of signatures of diamonds having a same shape and size of defects, may form cluster of signatures of diamonds having a same shape, location and size of defects, may form cluster of signatures of diamonds having a same location and size of defects, and the like).

The clusters may represent rules for grading. e.g. the closer it is to the middle the less valuable it is, or the bigger the defect is the less valuable it is.

The clusters may be partially unsupervised in the sense they are constraint by the grade assigned to the diamonds but this is be the only supervised aspect. The clustering process may find signatures of diamonds that share a unique feature in an unsupervised manner The clusters may be generated by Group all the signatures of diamonds associated with the same grade.

Perform an unsupervised clustering of the signatures of the diamonds of the same grade.

The cluster may be generated by

Clustering the signatures of all diamonds regardless the score (this can be done in an unsupervised manner).

Perform at least one clustering iteration until reaching clusters that includes signatures of the same grade. The clustering iteration may be applied only on clusters that are non homogenous.

In both cases the clusters may be unique in the sense that each cluster may represent a unique combination of grade and unique feature.

The clusters may be unique in the sense that a unique feature appears only in one of the clusters—regardless of the grade.

A diamond may be represented by a diamond signature (representing all parameters of the diamond—representing all of the first subset of parameter signatures) or by a partial signature (representing only some of the parameters of the diamond). The weight of the diamond may be part of the signature or may be regarded as metadata.

A cluster may include signature that are diamond signatures or partial diamond signatures.

The plurality of first signatures may form a single diamond signature. The subset may form a partial diamond signature.

Once a diamond signature (or a partial diamond signature) of a diamond is received the diamond signature (or a partial diamond signature) may be compared to the clusters to find a matching cluster—which is indicative of the grade to be provided to the diamond.

Non-limiting examples of a generation of a signature and of a generation of a cluster may be found in and may be listed below.

FIG. 1 illustrates a matching process.

It is assumed that there are multiple (M) cluster structures 24(1)-24(M). Each cluster (cluster structure) includes cluster signatures, metadata regarding the cluster signatures such as the weight of the diamond and grade.

For example—first cluster structure 24(1) includes multiple (N1) signatures (referred to as cluster signatures CS) CS(1,1)-CS(1,N1) 25(1,1)-25(1,N1), metadata 26(1).

Yet for another example—M'th cluster structure 24(M) includes multiple (N2) signatures (referred to as cluster signatures CS) CS(M,1)-CS(M,N2) 25(M,1)-25(M,N2), metadata 26(M).

The number of signatures per cluster structure may change over time—for example due to cluster reduction attempts during which a CS is removed from the structure to provide a reduced cluster structure, the reduced structure is checked to determine that the reduced cluster signature may still identify objects that were associated with the (non-reduced) cluster signature—and if so the signature may be reduced from the cluster signature.

The signatures of each cluster structures are associated to each other, wherein the association may be based on similarity of signatures and/or based on association between metadata (for example grade) of the signatures.

Assuming that each cluster structure is associated with a unique type of diamond—then diamonds may be graded by finding cluster structures that are associated with a certain grade. The finding of the matching cluster structures may include comparing a signature or partial signature of the diamond to signatures of the cluster structures—and searching for one or more matching signature out of the cluster signatures.

Figure 2:
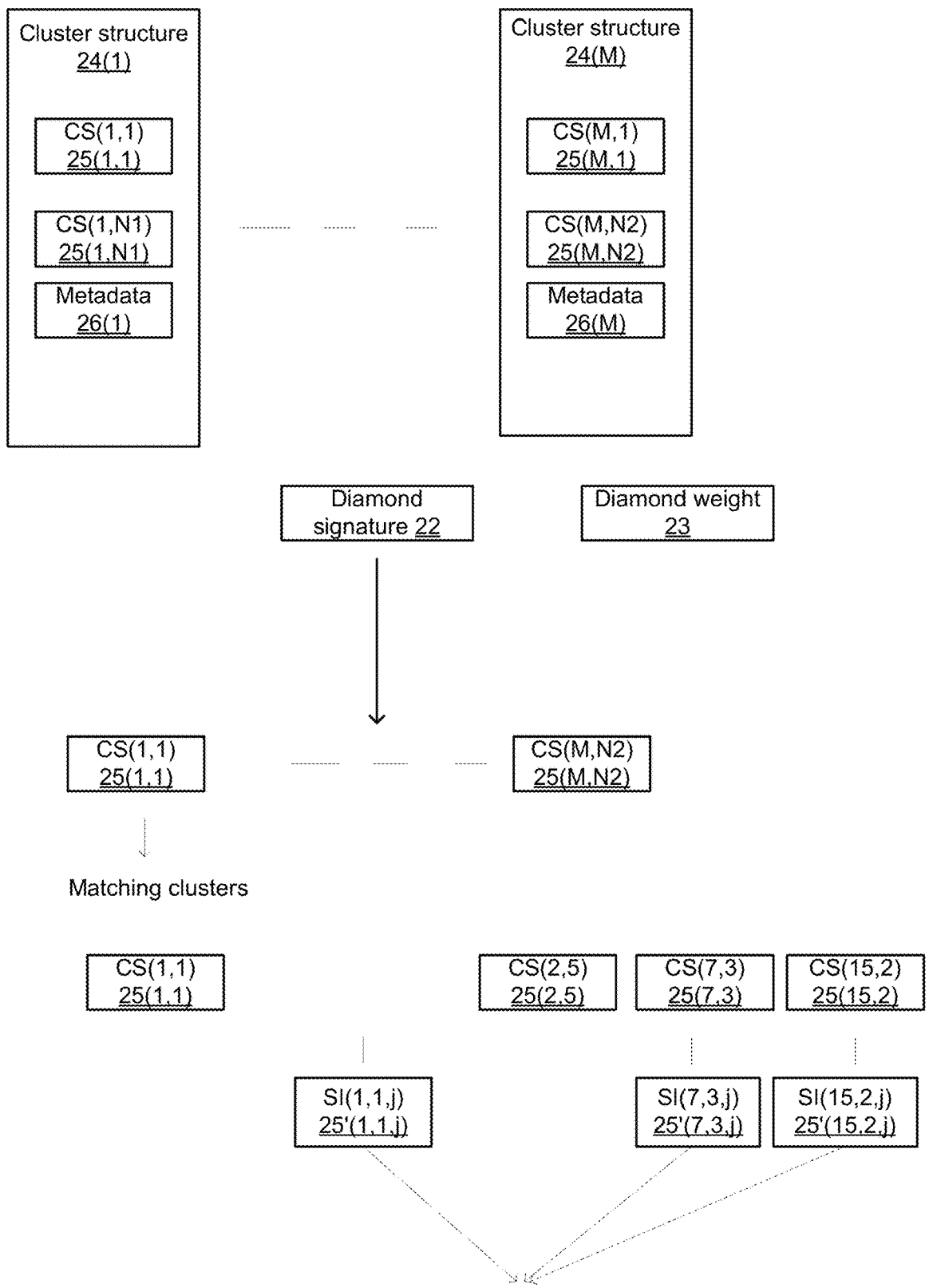
FIG. 2 illustrates an example of a method.

In FIG. 2—one or more images of a diamond undergoes a grading process. A diamond signature or a partial diamond signature is denoted 22. The diamond is also characterized by its weight 22.

The media unit signature 23 is compared to the signatures of the M cluster structures—from CS(1,1) 25(1,1) till CS(M,N2) 25(M,N2). The weight is also compared to weight metadata of the clusters.

We assume that one or more cluster structures are matching cluster structures.

Once the matching cluster structures are found the method proceeds by determining the grade of the diamond—based on the grade associated with the matching cluster.

It has been found that many diamond may be very similar to each other. For example—similar diamonds may be mined at a same location, at the same time, shaped (cut and polished) to the substantially the same shape and size. Similarity may arise regardless of time and location of mining.

There is a growing need to provide a diamond signature (a highly distinctive diamond signature) that may distinguish a diamond from similar diamonds.

There may be provide a method for generating a diamond signature. The method may include using diamond specific augmentations to simulate appearances under various conditions (multiple rotations, tilt, lighting, shadows, and even scratches).

The method may highlight the relevant indexes in the signature by taking the source stone signature, matching it to another example/s of the stone, identifying important IDs, and then taking the x closes matches that come from different stones—and removing IDs and were similar to IDs from the same stone.

The method may generate an adaptive threshold per stone to optimize the results (matching other examples of itself to other stones and finding the optimal match threshold in terms of number of signature IDs required to match).

The method may include training separate indexers to highlight (and get separate signatures) for different textures of the diamond—for example—one indexer to identify a crystal structure (shape), another indexer that highlights cracks and impurities and ignores crystal structure, another one for coloring identification (Basically, they said that the diamonds are identical if (a) have same crystal struct; (b) have same imperfections—cracks and impurities; and (c) have the same coloring). The idea is to create 3 indexers for each of these aspects, create signature for each of these aspects, and measure similarity by each of these aspects, then, diamonds are identical if all 3 signatures are similar enough.

Figure 3:
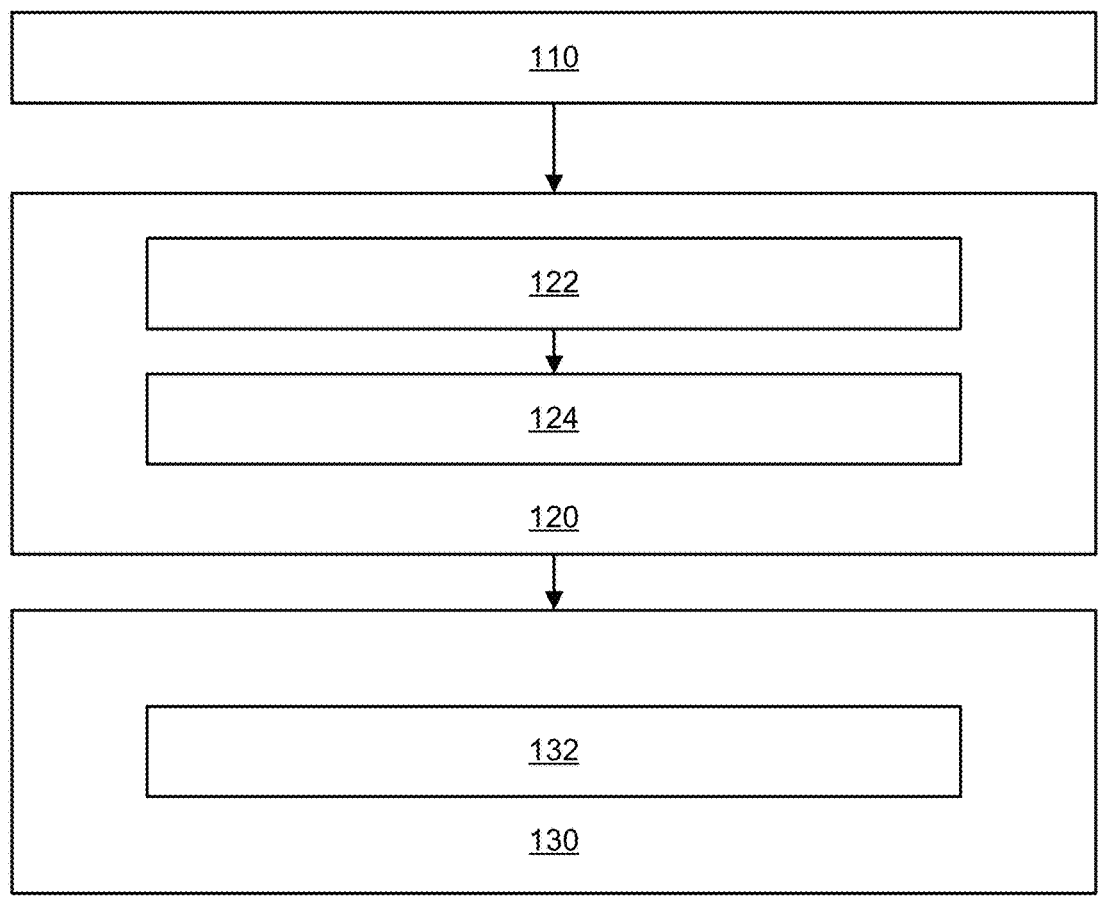
FIG. 3 illustrates an example of a method.

FIG. 3 illustrates method 100.

Method 100 is for generating a highly distinctive signature of a certain precious gem.

Method 100 may start by step 110 of generating, based on one or more images of the certain precious gem, a certain precious gem signature of the certain precious gem.

Step 110 may be followed by step 120 of finding, out of a group of reference precious gems, other precious gems having other precious gem signatures. The finding may include calculating similarities between the certain precious gem signature and reference precious gem signatures of the reference precious gems of the group.

Step 120 may be followed by step 130 of generating a new certain precious gem signature that significantly differs from signatures of the other precious gems.

Referring to step 110—the certain precious gem signature may include indexes that point to features of the one or more images of the certain precious gem. See, for example indexes ID1-ID5 of image signature 47 of FIG. 4.

Step 120 may include finding, out of the group of reference precious gems, best matching reference precious gems that are more similar to the certain precious gem than other reference precious gems of the group.

The finding of the other precious gems is may be followed by searching (141) for at least one non-distinctive index of the certain precious gem signature that does not differentiate the certain precious gem from the best matching reference precious gems. The searching may be included in step 130.

Step 130 may include removing (132) the at least one non-distinctive index from the at least one non-distinctive index.

Step 120 may include step 122 of calculating of similarity between the certain precious gem signature and a reference precious gem signature of a reference precious gem of the group by counting a number of indexes that appear in both the certain precious gem signature and the reference precious gem signature.

Step 120 may include step 124 of determining a similarity threshold that associated with the certain precious gem, as a minimal number of indexes that appear in the certain precious gem signature and in a signature of a precious gem compared to the certain to the certain precious gem signature.

For example—assuming that the X'th (X ranges between 1 and the size of the group of the best matching diamond signatures) best matching diamond signature shares Y indexes with the certain diamond signature—than in future searches (in which the certain diamond signature is compared to a signature of another diamond)—Y may be used as a threshold to determine if the certain diamond and the other diamond match.

It should be noted that one or more certain diamond signatures may be generated based on one or more images of the diamond. An image may be a real image, a processed real image, a synthetic image, a simulated image, and the like.

Images of the certain diamond may represent may images acquired at different image acquisition parameters and/or at may represent estimates on appearances of the diamond at different points in time.

Estimates on the appearances of the diamond at different points in time may estimate how the certain diamond changed over time and/or how it will change in the future. The change may include adding scratches and/or the result of any other chemical and/or mechanical event applied on the diamond.

Different image of the certain diamond be generated in various manners—for example estimating different imaging directions, different imaging angles, different illumination conditions, and the like.

If an image from a certain angle is not available—the method may estimate the image based on certain angle images of similar diamonds.

When there are more than a single certain diamond signature (or when the signature is generated based on different images) then method 100 may be executed per one or more of the certain diamond signatures and/or per image.

In such a case—method 100 may include clustering the multiple certain diamond signatures of the certain diamond to provide a certain diamond cluster.

Method 100 may generate signatures—for example by the methods illustrated in U.S. patent application Ser. No. 16/542,327 filing date Aug. 16 2019, which is incorporated herein by reference.

Figure 4:
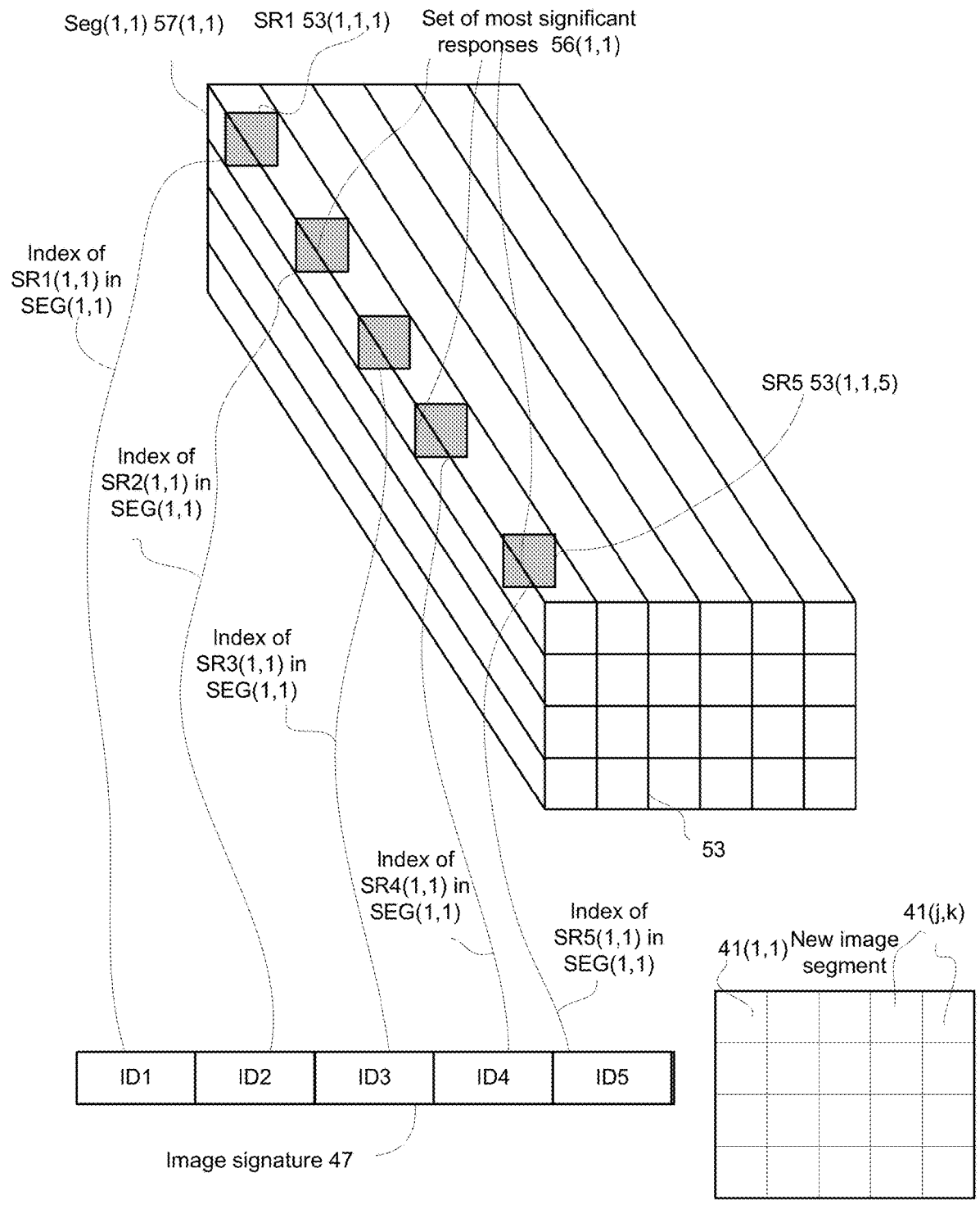
FIG. 4 is an example of a signature of a media unit that is an image, and of an outcome of a last (K'th) iteration.
Figure 5:
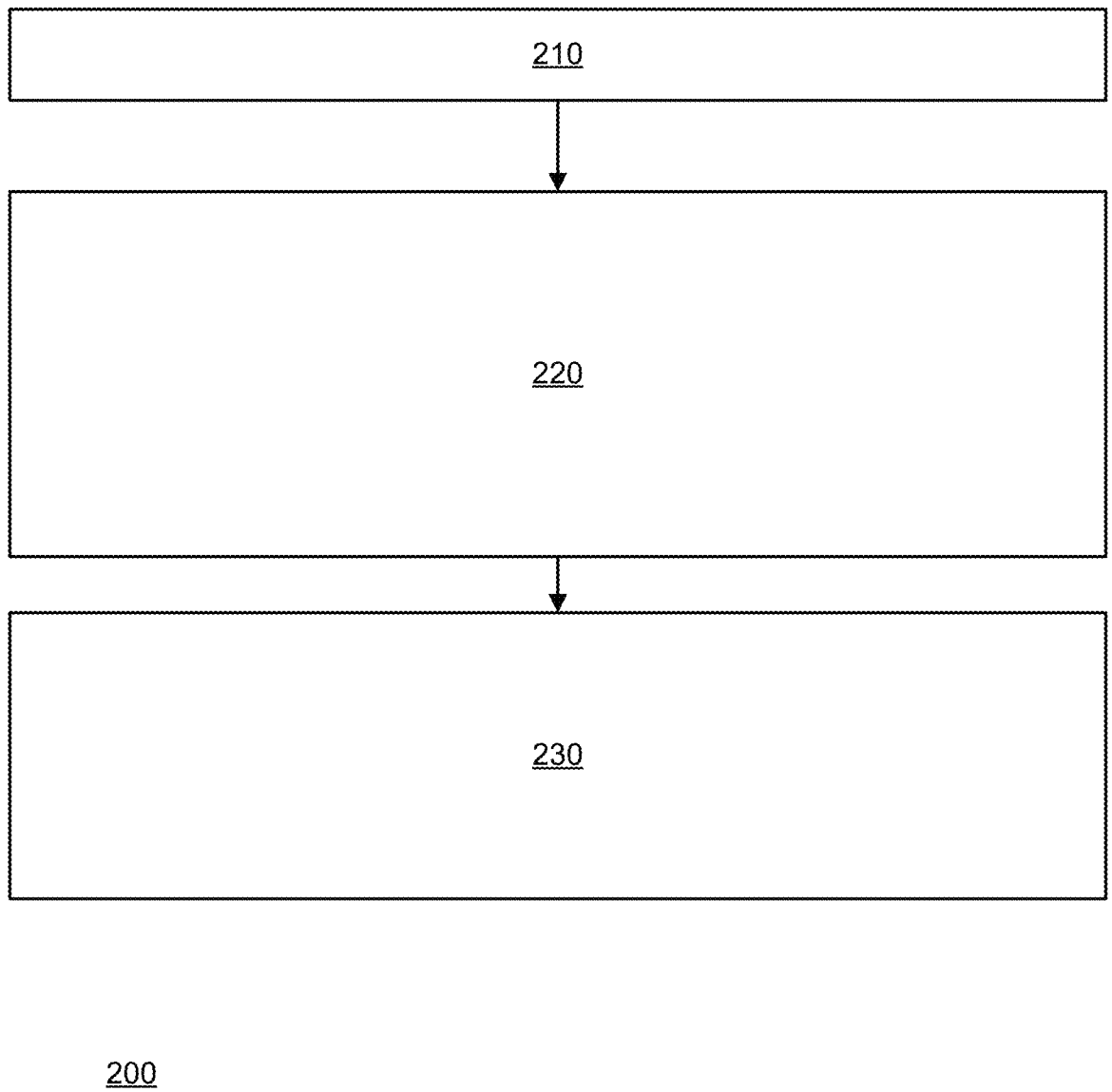
FIG. 5 illustrates an example of a method.

FIG. 4 is an example of a signature 77 of a media unit that is an image 40 and of an outcome 53 of the last (K'th) iteration.

The image 41 is virtually segments to segments 40($i,k$). The segments may be of the same shape and size but this is not necessarily so.

Outcome 53 may be a tensor that includes a vector of values per each segment of the media unit. One or more objects may appear in a certain segment. For each object— an object identifier (of the signature) points to locations of significant values, within a certain vector associated with the certain segment.

For example—a top left segment (41(1,1)) of the image may be represented in the outcome 53 by a vector V(1,1) 57(1,1) that has multiple values. The number of values per vector may exceed 100, 200, 500, 1000, and the like.

The significant values (for example—more than 10, 20, 30, 40 values, and/or more than 0.1%, 0.2%. 0.5%, 1%, 5% of all values of the vector and the like) may be selected. The significant values may have the values—but may be selected in any other manner FIG. 4 illustrates a set of significant responses 55(1,1) of vector V(1,1) 57(1,1). The set includes five significant values (such as first significant value SV1(1,1) 53(1,1,1), second significant value SV2(1,1), third significant value SV3(1,1), fourth significant value SV4(1,1), and fifth significant value SV5(1,1) 53(1,1,5)).

The image signature 77 includes five indexes for the retrieval of the five significant values—first till fifth identifiers ID1-ID5 are indexes for retrieving the first till fifth significant values.

FIG. 7 illustrates an example of method 200.

Method 200 is a computerized method for determining a grade of a precious gem.

Method 200 may start by step 210 of generating, by a signature generator, a signature of the precious gem.

Step 210 may be followed by step 220 of searching, out of multiple concept structures, for a matching concept structures that comprises at least one reference signature that matches the signature of the precious gem.

Each concept structure comprises precious gem signatures of the same grade; wherein at least two concept structures differ from each other by grade; wherein each concept structure is generated by applying an unsupervised learning process and associating a grade with the cluster.

Step 220 may be followed by step 230 of determining the grade of the precious gem based on a grade associated with a matching concept structure.

Each concept structure may be associated with a unique grade that differs from grades of other concept structures.

The signature of the precious gem may be indicative of at least one out of cut, color, and clarity.

The signature of the precious gem may be indicative of at least two out of cut, color, and clarity.

The signature of the precious gem may be indicative of cut, color, and clarity.

One or more concept structures may include reference signatures of a same precious gem obtained under different image acquisition parameters.

One or more concept structures may include reference signatures of a same precious gem obtained under different angles of view.

One or more concept structures may include reference signatures of a same precious gem obtained at different points in time.

The method may include generating the multiple concept structures.

The generating may include clustering, in a supervised manner, reference signatures of a same grade to provide the multiple concept structures.

Each cluster may include reference signatures that are of a same unique combination of grade and at least one precious gem property.

The at least one precious gem property may be at least one out of cut, color, and clarity.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It is appreciated that various features of the embodiments of the disclosure which are, for clarity, described in the contexts of separate embodiments may also be provided in combination in a single embodiment. Conversely, various features of the embodiments of the disclosure which are, for brevity, described in the context of a single embodiment may also be provided separately or in any suitable sub-combination.

It will be appreciated by persons skilled in the art that the embodiments of the disclosure are not limited by what has been particularly shown and described hereinabove. Rather the scope of the embodiments of the disclosure is defined by the appended claims and equivalents thereof.

We claim:

1. A method for generating a highly distinctive signature of a certain precious gem, the method comprises:
    sensing, by an image sensor, an image of the certain precious gem;
    generating, based on the image of the certain precious gem, a certain precious gem signature of the certain precious gem; wherein the certain gem signature comprises indexes for retrieving elements of a tensor that is generated in response to the sensing of the image of the certain precious gem, the tensor comprises multiple values per each image segments of multiple image segments of the image of the certain precious gem;
    finding, out of a group of reference precious gems, other precious gems having other precious gem signatures; wherein the finding comprises calculating similarities between the certain precious gem signature and reference precious gem signatures of the reference precious gems of the group; wherein a similarity between the certain precious gem signature and any reference precious gem signature is determined based a number of indexes of a same value that appear in the certain precious gem signature and in the reference precious gem signature; and
    generating a new certain precious gem signature that significantly differs from signatures of the other precious gems; wherein the generating comprises removing from the certain precious gem signature at least one non-distinctive index that does not differentiate the certain precious gem from best matching reference precious gems, the best matching reference precious gems are selected of the group of reference precious gems and are more similar to the certain precious gem than other reference precious gems of the group.

2. The method according to claim 1, comprising finding, out of the group of reference precious gems, the best matching reference precious gems.

3. The method according to claim 2, comprising searching for the at least one non-distinctive index of the certain precious gem signature.

4. The method according to claim 2, wherein the similarity between the certain precious gem signature and any reference precious gem signature is determined by counting a number of the indexes that appear in both the certain precious gem signature and the reference precious gem signature.

5. The method according to claim 4, comprising determining a similarity threshold that associated with the certain precious gem, wherein the similarity threshold is a minimal number of indexes that appear in the certain precious gem signature and also appear in a reference signature of a precious gem that is compared to the certain precious gem signature.

6. The method according to claim 5, wherein the determining of the similarity threshold is based on a similarity between the certain precious gem signature and at least one reference precious gem signature of at least one of the best matching reference precious gems.

7. The method according to claim 2, wherein a number of best matching reference precious gems is predefined.

8. The method according to claim 2, comprising sensing by the image sensor multiple images of the certain precious gem; and generating, based the multiple images of the certain precious gem, multiple certain precious gem signatures of the certain precious gem.

9. The method according to claim 8 comprising applying different image acquisition parameters when sensing at least two of the multiple certain precious gem images.

10. The method according to claim 8, wherein at least two of the multiple certain precious gem signatures of the certain precious gem are acquired at different points in time.

11. The method according to claim 8, wherein the image sensor is a visible light sensor.

12. The method according to claim 8, comprising clustering the multiple certain precious gem signatures of the certain precious gem to provide a certain precious gem cluster.

13. The method according to claim 8, wherein the image sensor is an x-ray sensor.

14. The method according to claim 1, comprising generating one or more additional signatures of the certain precious gem based on one or more estimates of one or more appearances of the precious gem at one or more different points in time, wherein the one or more estimates are generated by an addition of scratches.

15. A non-transitory computer readable medium for generating a highly distinctive signature of a certain precious gem, the non-transitory computer readable medium stores instructions for:

sensing, by an image sensor, an image of the certain precious gem;

generating, based on the image of the certain precious gem, a certain precious gem signature of the certain precious gem; wherein the certain gem signature comprises indexes for retrieving elements of a tensor that is generated in response to the sensing of the image of the certain precious gem, the tensor comprises multiple values per each image segments of multiple image segments of the image of the certain precious gem;

finding, out of a group of reference precious gems, other precious gems having other precious gem signatures; wherein the finding comprises calculating similarities between the certain precious gem signature and reference precious gem signatures of the reference precious gems of the group; wherein a similarity between the certain precious gem signature and any reference precious gem signature is determined based a number of indexes of a same value that appear in the certain precious gem signature and in the reference precious gem signature; and generating a new certain precious gem signature that significantly differs from signatures of the other precious gems; wherein the generating comprises removing from the certain precious gem signature at least one non-distinctive index that does not differentiate the certain precious gem from best matching reference precious gems, the best matching reference precious gems are selected of the group of reference precious gems and are more similar to the certain precious gem than other reference precious gems of the group.

* * * * *